United States Patent [19]

Gibby

[11] Patent Number: 4,933,441

[45] Date of Patent: Jun. 12, 1990

[54] CONTRAST ENHANCING AGENTS FOR MAGNETIC RESONANCE IMAGES

[76] Inventor: Wendell A. Gibby, 695 E. 1700 North, Mapleton, Utah 84664

[21] Appl. No.: 339,143

[22] Filed: Apr. 17, 1989

Related U.S. Application Data

[63] Continuation-in-part of Ser. No. 7,289, Jan. 27, 1987, Pat. No. 4,822,594.

[51] Int. Cl.$^5$ .................. A61K 49/00; A61B 6/00; C08B 37/02
[52] U.S. Cl. .................................. 536/112; 424/1.1; 424/9; 128/653; 128/654
[58] Field of Search ............... 424/9, 1.1; 536/112; 128/653, 654

[56] References Cited

U.S. PATENT DOCUMENTS 4,822,594 4/1989 Gibby ....................... 424/9

Primary Examiner—Ronald W. Griffin
Attorney, Agent, or Firm—Drucker & Sommers

[57] ABSTRACT

A nonionic contrast enhancing agent for magnetic resonance. In a preferred embodiment a chelating agent, for example, EDTA or DTPA, binds a metal, preferably Gd, having at least one unpaired electron. Any carboxyl groups not involved in chelation are bound to a reduced lower carbohydrate having between 3 and 5 carbon atoms. Such compositions are useful for enhancing the contrast of Magnetic Resonance images.

4 Claims, No Drawings

CONTRAST ENHANCING AGENTS FOR MAGNETIC RESONANCE IMAGES

This application is a continuation-in-part of Ser. No. 07/007,289, filed Jan. 27, 1987, now Pat. No. 4,822,594.

BACKGROUND OF THE INVENTION

1. Field of the Invention

This invention relates to NMR shift reagents and in particular contrast enhancing agents for magnetic resonance imaging.

2. Prior Art

Magnetic Resonance (hereinafter MR) imaging is one of the newest methods of viewing the interior of the human body. Radio waves interact with protons in a magnetic field to produce images having superior contrast compared to X-ray tomography. However, the technique can be non-specific, that is, it may be impossible to distinguish from between many pathological conditions, such as between cancer and the edema surrounding the cancer.

Contrast agents enhance various portions of the MR image by changing, usually decreasing, the relaxation times of the protons in the immediate vicinity to the agent. One example of a contrast agent is that disclosed in the European Patent 3,302,410 of A. G. Schering for gadolinium diethyline triamine pentaacetic acid complex (hereinafter Gd DTPA). Gd DTPA has been attached to a variety of macromolecules, for example monoclonal antibodies, albumin, and dihexadecylamine.

Other agents, such as ethylene diamine tetraacetic acid (hereinafter EDTA), and 1, 4, 7, 10 tetraacetic acid (hereinafter DOTA), have been chelated with Gd in an effort to make a superior contrast agent.

Prior art chelates of Gd, and other paramagnetic metals, suffer from several defects. The body rapidly excretes Gd DTPA, for example. It is not organ specific and stays within the extra-cellular space. As a result, the only organs suitably enhanced with Gd DTPA are kidneys and areas of abnormal brain permeability. Since magnetic resonance imaging requires long data acquisition times rapidly metabolized enhancing agents do not work well.

Another problem with known MR enhancing agents is that the proteins that are used to anchor the simple chelates, monoclonal antibodies and the like, may provoke allergic reactions in the recipient.

It would therefore be advantageous to have a MR contrast enhancing agent that was metabolized slowly in vivo, was organ specific, and did not provoke allergic reactions in the recipient.

SUMMARY OF THE INVENTION

A nonionic contrast enhancing agent for magnetic resonance. In a preferred embodiment a chelating agent, for example, EDTA or DTPA, binds a metal, preferably Gd, having at least one unpaired electron. Any carboxyl groups not involved in chelation are bound to a reduced lower carbohydrate having between 3 and 5 carbon atoms. Such compositions are useful for enhancing the contrast of Magnetic Resonance images.

A magnetic resonance contrast enhancing agent comprising a chelating agent represented by the formula A:

FORMULA A $$Y-\left[\begin{array}{c}(CH_2)_p COOH \\ | \\ N-(CH_2)_n \end{array}\right]_m - N\begin{array}{c}X \\ \diagdown \\ (CH_2)_p COOH\end{array}$$

where m is 1, 2, or 3;

n is an interger between 1 and 4;

p can be independently varied and is an integer between 0 and 2; and

X and Y can be $-(CH_2)_p$ COOH or X is $(CH_2)_n$ and joined to Y;

at least one reduced lower carbohydrate bound to said chelating agent through an ester linkages of one of said (COOH) groups and (OH) groups of the reduced lower carbohydrate; and a metal ion having at least one unpaired electron chelated to a compound of formula A, provided that all (COOH) groups not involved in metal chelation are bound to a reduced lower carbohydrate.

DETAILED DESCRIPTION OF THE INVENTION

This is a continuation-in-part of U.S. patent application 007,289 now U.S. Pat. No. 4,822,594, which disclosure is incorporated herein in full.

The magnetic resonance contrast enhancing agents of this invention include a chelating agent represented by the formula A:

FORMULA A $$Y-\left[\begin{array}{c}(CH_2)_p COOH \\ | \\ N-(CH_2)_n \end{array}\right]_m - N\begin{array}{c}X \\ \diagdown \\ (CH_2)_p COOH\end{array}$$

where m is 1, 2, or 3;

n is an interger between 1 and 4;

p can be independently varied and is an integer between 0 and 2; and

X and Y can be $-(CH_2)_p$ COOH or X is $(CH_2)_n$ and joined to Y;

Examples of chelating agents in this category include DTPA (where m is 2, n is 2, each p is 1 and x and y are $-(CH_2)_p$ COOH); EDTA (where m is 0, n is 2, and each p is 1 and x and y are $-(CH_2)_p$ COOH) and DOTA (where m is 3, n is 2, each p is 1, x is $-(CH_2)_2-$ and joined to y. These agents are known to tenaciously bind metal ions. They can be used to place otherwise toxic metal ions in organic environments, particularly biological environments by coordinating with the metal ion and thus preventing it from poisoning critical membranes or enzymes.

As used herein "reduced lower carbohydrate" will refer to compounds having 3, 4, or 5 carbon atoms, each primary or secondary carbon atom having a hydroxyl group. Such compounds include glycerol, adonitol, arabinol, erythitol, pentaerythritol, and xylitol. A reduced lower carbohydrate will not have any carbonyl functionallity.

As used herein, "chelate/reduced lower carbohydrate" will refer to the compounds formed by the reaction of the above described chelates with the above described reduced lower carbohydrates. The carboxoyl or (COOH) groups at the various terminii of the chelating agent can react with the hydroxyl or (OH) groups on the reduced lower carbohydrate, thereby forming ester linkages. Since the chelate has more that one (COOH) group and the reduced lower carbohydrate have more than one (OH) group, large cross linked polymers may be formed. In the compounds of this invention the carboxoyl groups will be involved in chelation of the metal ion or will be esterified to a lower carbohydrate.

Metal ions easily bind to the chelate/reduced lower carbohydrate. Preferred metal ions include those having at least one unpaired electron, which is to say, those that are paramagnetic. Examples include Cr, Mn, Fe, Co, and the lanthanide metals, particularly Gd, Dy, and Tc.

The metal complexes of the chelate/reduced lower carbohydrates can then be used as contrast enhancers for MR images. The method of administration of the complex, depends on the portion of the anatomy to be imaged. For example, if the gastrointestinal tract is to be imaged, oral administration is preferred. For imaging of the liver, spleen, and kidneys, intravenous administration is preferred.

Various formulations of the metal chelate/reduced lower carbohydrate will have different physical properties. For example, highly cross-linked polymeric chelate/reduced lower carbohydrate will be fairly insoluble particles, but less highly cross linked polymers are more soluble. The amount of cross linking can be controlled by the ratio of chelate to reduced lower carbohydrate. The ratio will range from about 2:1 to about 1:50. In general, the more chelate present the more the product will be cross linked.

Another physical variable that can be controlled is the size, or molecular weight, of the reduced lower carbohydrate. Small reduced lower carbohydrates, such as mono reduced lower carbohydrates and oligo reduced lower carbohydrates, produce more easily soluble chelate/reduced lower carbohydrate. Larger reduced lower carbohydrates, such as high molecular weight dextran, or starch, produce more insoluble chelate/reduced lower carbohydrate.

The clinician can use the various properties to his advantage. For example, if the area to be imaged includes delicate vascular systems, for example, the liver, or brain, a highly soluble form of metal chelate/reduced lower carbohydrate is preferred. If double contrast images of gastrointestinal tract are preferred, then more insoluble form of metal chelate/reduced lower carbohydrate that coats the interior surface of the organs is preferred.

The chelate/reduced lower carbohydrate can also be used for ion exchange column packing. The physical properties of the chelate can be varied to more favorably bind one metal ion than another, thereby giving the column the desired discrimination.

METHODS OF PREPARATION

The chelate/reduced lower carbohydrates of the present invention are prepared as follows:

The chelate-bisanhydride is prepared by adding dry chelate to an anhydrous organic base, for example, pyridine, lutidine, piperidine, or the like. The resulting slurry is stirred and an anhydrous organic acid, for example, acetic acid or pentanoic acid, is slowly added.

The mixture is heated to between about 45° C. to about 85° C. preferably about 65° C. and left for between 12 hours and 48 hours preferably about 20 hours. The liquid is filtered, and the solid material is washed with the same organic acid used before.

The ratio of chelate to reduced lower carbohydrate ranges from 2:1 to 1:50 when the reduced lower carbohydrate is calculated as glucose. The average number of glucose units in a given polymer must therefore be known. The reduced lower carbohydrate and the chelate are mixed dry in, for example, a beaker. Anhydrous dimethyl sulfoxide (DMSO) is added to the thoroughly mixed dry mixture.

The next step provides a choice of physical properties depending on whether a gel-like consistency is desired or if fine particles are desired.

The gel is obtained by warming the DMSO mixture until the particles go into solution. Typically this temperature is from 40° C. to 70° C. The gel is purified by dialysis in water.

Particles are obtained by pulverizing the mixture with a homogenizer. The homogenized mixture is let stand for several hours, then the supernatant is decanted off.

After the chelate/reduced lower carbohydrate is obtained, a metal ion can be added to form a complex. A metal halide, for example gadolinium chloride, is added to an aqueous suspension, and the mixture is mixed well. After dialysis, the resulting solid is dried.

EXAMPLE

The synthesis of DPTA:2glycerol:gadolinium 5 grams of DPTA is added to a molar excess of glycerol in DMSO. The mixture is heated to 80° C. After all the product is dissolved, the reaction mixture is filtered through #2 Watman filter paper and 300 cc of absolute ethanol is added. The product is removed and washed with $3 \times 100$ cc absolute ethanol and $1 \times 100$ cc water.

The product is chelated with gadolinium III chloride at pH 5.8 with xyenol orange as indicator. The indicator is removed by passing the chelate through an ion exchange column.

I claim:

1. A magnetic resonance contrast enhancing agent comprising a chelating agent represented by the formula A:

$$Y\left[\begin{array}{c}(CH_2)_p COOH \\ | \\ N-(CH_2)_n- \end{array}\right]_m N\begin{array}{c}X \\ \diagdown \\ (CH_2)_p COOH\end{array} \quad \text{FORMULA A}$$

where m is 1, 2, or 3;

n is an integer between 1 and 4;

p can be independently varied and is an integer between 0 and 2; and

X and Y can be $-(CH_2)_p$ COOH or X is $(CH_2)_n$ and joined to Y;

at least one carbohydrate selected from glycerol, adonitol, arabitol, erythritol, pentaerythritol, xylitol bound to said chelating agent through an ester linkages of one of said (COOH) groups and (OH) groups of the carbohydrate; and a metal ion having at least one unpaired electron chelated to a compound of formula A, provided that all (COOH) groups not involved in metal chelation are bound to a carbohydrate.

2. The magnetic resonance contrast enhancing agent of claim 1 wherein a component of formula A is selected from the group of EDTA, DTPA, and DOTA.

3. The magnetic resonance contrast enhancing agent of claim 1 wherein said metal ion is selected from the lanthanide group of metals.

4. The magnetic resonance contrast enhancing agent of claim 3 wherein said metal ion is Gd.

* * * * *